US011653995B2

(12) United States Patent
Eddy

(10) Patent No.: US 11,653,995 B2
(45) Date of Patent: *May 23, 2023

(54) ANTIMICROBIAL TREATMENT FOR A SURGICAL HEADLAMP SYSTEM

(71) Applicant: Parasol Medical, LLC, Buffalo Grove, IL (US)

(72) Inventor: Patrick E. Eddy, Allendale, MI (US)

(73) Assignee: Parasol Medical, LLC, Buffalo Grove, IL (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/091,522

(22) Filed: Nov. 6, 2020

(65) Prior Publication Data

US 2021/0052345 A1 Feb. 25, 2021

Related U.S. Application Data

(63) Continuation of application No. 15/938,934, filed on Mar. 28, 2018, now Pat. No. 10,864,058.

(51) Int. Cl.
  *A61B 90/30* (2016.01)
  *F21V 21/084* (2006.01)
  (Continued)

(52) U.S. Cl.
  CPC ............ *A61B 90/30* (2016.02); *F21V 21/084* (2013.01); *A61B 90/36* (2016.02); *A61L 2300/404* (2013.01); *F21L 14/00* (2013.01)

(58) Field of Classification Search
  CPC ....... A61B 90/30; A61B 90/36; A61B 90/361; F21V 21/08; F21V 21/084; F21L 14/00
  See application file for complete search history.

(56) References Cited

U.S. PATENT DOCUMENTS

| 3,241,152 A | 3/1966 | Hay |
| 3,515,131 A | 6/1970 | Stevens |

(Continued)

FOREIGN PATENT DOCUMENTS

| EP | 0108853 A1 | 5/1984 |
| EP | 0129980 A2 | 1/1985 |

(Continued)

OTHER PUBLICATIONS http://www.ncbi.nlm.nih.gov/pubmed/7753434, 1995 [retrieved on Dec. 4, 2012].

(Continued)

*Primary Examiner* — Christopher J Beccia
(74) *Attorney, Agent, or Firm* — Price Heneveld LLP

(57) ABSTRACT

A surgical headlight system has a headlamp. The surgical headlight system can further include a headwear structure, configured to be worn on a surgeon's head during surgery, supporting the headlamp. The surgical headlight system can further include a video camera configured to record surgery. The headlamp, the headwear structure and the video camera all have an exterior surface. An antimicrobial coating is applied to the exterior surface of the headlamp, the exterior surface of the video camera, and/or the exterior surface of the headwear structure. The antimicrobial coating includes a silane quaternary ammonium ion or salt thereof. The antimicrobial coating imparts antimicrobial properties onto the exterior surface to which it is applied, such as the exterior surface of the headlamp. The silane quaternary ammonium ion or salt thereof can be one or more of 3-(trimethoxysilyl) propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

20 Claims, 4 Drawing Sheets

(51) Int. Cl.
*A61B 90/00* (2016.01)
*F21L 14/00* (2006.01)

(56) References Cited

U.S. PATENT DOCUMENTS

| | | | |
|---|---|---|---|
| 3,654,165 A | 4/1972 | Bryant et al. | |
| 4,017,662 A | 4/1977 | Gehman et al. | |
| 4,266,669 A | 5/1981 | Watson | |
| 4,372,303 A | 2/1983 | Grossmann et al. | |
| 4,394,378 A | 7/1983 | Klein | |
| 4,414,268 A | 11/1983 | Baldwin | |
| 4,504,541 A | 3/1985 | Yasuda et al. | |
| 4,603,152 A | 7/1986 | Laurin et al. | |
| 4,735,198 A | 4/1988 | Sawa | |
| 4,797,420 A | 1/1989 | Bryant | |
| 4,865,844 A | 9/1989 | Blank et al. | |
| 4,891,846 A | 1/1990 | Sager et al. | |
| 4,921,691 A | 5/1990 | Stockel | |
| 5,003,970 A | 4/1991 | Parker et al. | |
| 5,079,004 A | 1/1992 | Blank et al. | |
| 5,183,664 A | 2/1993 | Ansell | |
| 5,193,549 A | 3/1993 | Bellin et al. | |
| 5,270,358 A | 12/1993 | Asmus | |
| 5,277,698 A | 1/1994 | Taylor | |
| 5,411,585 A | 5/1995 | Avery et al. | |
| 5,428,078 A | 6/1995 | Cohen et al. | |
| 5,466,898 A | 11/1995 | Gilbert et al. | |
| 5,520,664 A | 5/1996 | Bricault, Jr. et al. | |
| 5,592,946 A | 1/1997 | Eddy | |
| 5,620,001 A | 4/1997 | Byrd et al. | |
| 5,660,182 A | 8/1997 | Kuroshaki et al. | |
| 5,685,866 A | 11/1997 | Lopez | |
| 5,762,623 A | 6/1998 | Murphy et al. | |
| 5,954,869 A | 9/1999 | Elfersy et al. | |
| 5,959,014 A | 9/1999 | Liebeskind et al. | |
| 6,186,957 B1 | 2/2001 | Milam | |
| 6,221,944 B1 | 4/2001 | Liebeskind et al. | |
| 6,224,579 B1 | 5/2001 | Modak et al. | |
| 6,344,025 B1 | 2/2002 | Inagaki et al. | |
| 6,420,455 B1 | 7/2002 | Landgrebe et al. | |
| 6,492,012 B1 | 12/2002 | Shah | |
| 6,495,229 B1 | 12/2002 | Carte et al. | |
| 6,520,281 B1 | 2/2003 | Deslauriers et al. | |
| 6,575,917 B2 | 6/2003 | Giroux et al. | |
| 6,738,986 B1 | 5/2004 | Martin | |
| 6,803,034 B2 | 10/2004 | DuVal et al. | |
| 6,821,936 B2 | 11/2004 | Green et al. | |
| 6,821,943 B2 | 11/2004 | Avery et al. | |
| 6,822,030 B2 | 11/2004 | Olson et al. | |
| 6,994,890 B2 | 2/2006 | Ohlhausen et al. | |
| 7,045,673 B1 | 5/2006 | Batich et al. | |
| 7,081,101 B1 | 7/2006 | Sawa | |
| 7,201,914 B2 | 4/2007 | Dees | |
| 7,645,824 B2 | 1/2010 | Hendriks et al. | |
| 7,674,473 B2 | 3/2010 | Falder et al. | |
| 7,704,313 B2 | 4/2010 | Ohlhausen et al. | |
| 7,709,694 B2 | 5/2010 | Batich et al. | |
| 7,731,564 B2 | 6/2010 | Sanders | |
| 7,754,004 B2 | 7/2010 | Ohlhausen et al. | |
| 7,754,625 B2 | 7/2010 | Hendriks et al. | |
| 7,790,217 B2 | 9/2010 | Toreki et al. | |
| 8,025,120 B2 | 9/2011 | Eddy | |
| 8,178,484 B2 | 5/2012 | Schwarz et al. | |
| 8,257,780 B2 | 9/2012 | Ohlhausen et al. | |
| 8,440,217 B1 | 5/2013 | El-Naggar et al. | |
| 8,449,483 B2 | 5/2013 | Eddy | |
| 8,491,922 B2 | 7/2013 | Eddy | |
| 8,574,844 B2 | 11/2013 | Burkhardt, III et al. | |
| 8,639,527 B2 | 1/2014 | Rensvold et al. | |
| 8,679,526 B2 | 3/2014 | Van Den Plas et al. | |
| 8,916,742 B2 | 12/2014 | Smith | |
| 8,956,665 B2 | 2/2015 | Bolkan et al. | |
| 8,999,363 B2 | 4/2015 | Elfersy | |
| 9,028,846 B2 | 5/2015 | Eddy | |
| 9,089,138 B2 | 7/2015 | Higgins et al. | |
| 9,095,731 B2 | 8/2015 | Gentle et al. | |
| 9,149,393 B2 | 10/2015 | Cumming et al. | |
| 9,204,677 B2 | 12/2015 | Abbey et al. | |
| 9,215,903 B2 | 12/2015 | Abbey et al. | |
| 9,254,591 B2 | 2/2016 | Fox et al. | |
| 9,375,346 B1 | 6/2016 | Sundheimer et al. | |
| 9,433,708 B2 | 9/2016 | Eddy | |
| 9,675,735 B2 | 6/2017 | Eddy | |
| 9,717,249 B2 | 8/2017 | Eddy | |
| 9,757,769 B2 | 9/2017 | Grossman et al. | |
| 9,795,141 B2 | 10/2017 | Chason et al. | |
| 9,795,177 B1 | 10/2017 | Weaver | |
| 9,834,874 B2 | 12/2017 | Stein | |
| 9,840,626 B2 | 12/2017 | Farrugia et al. | |
| 9,845,569 B2 | 12/2017 | Dunn et al. | |
| 9,855,584 B2 | 1/2018 | Grossman et al. | |
| 9,877,875 B2 | 1/2018 | Eddy | |
| 9,877,879 B2 | 1/2018 | Beck | |
| 9,943,135 B2 | 4/2018 | Baychar | |
| 10,039,683 B2 | 8/2018 | Jung et al. | |
| 10,045,536 B2 | 8/2018 | Chason et al. | |
| 10,212,932 B2 | 2/2019 | Chiattello et al. | |
| 10,258,046 B2 | 4/2019 | Grossman et al. | |
| 10,258,411 B1* | 4/2019 | Ferguson | H04N 5/77 |
| 10,388,143 B2 | 8/2019 | Eddy et al. | |
| 10,470,689 B2 | 11/2019 | Kilcran et al. | |
| 10,472,157 B1 | 11/2019 | Dudding et al. | |
| 10,528,411 B2 | 1/2020 | Kucera et al. | |
| 10,758,426 B2 | 9/2020 | Eddy | |
| 10,822,502 B2 | 11/2020 | Eddy | |
| 10,864,058 B2* | 12/2020 | Eddy | A61B 90/30 |
| 10,967,082 B2 | 4/2021 | Eddy | |
| 2002/0111282 A1 | 8/2002 | Charaf et al. | |
| 2002/0170771 A1 | 11/2002 | Milam et al. | |
| 2003/0073600 A1 | 4/2003 | Avery et al. | |
| 2004/0019286 A1 | 1/2004 | Lia et al. | |
| 2004/0151919 A1 | 8/2004 | Bagwell et al. | |
| 2004/0166173 A1 | 8/2004 | Albach | |
| 2005/0008763 A1 | 1/2005 | Schachter | |
| 2005/0035164 A1 | 2/2005 | Badillo | |
| 2005/0187580 A1 | 8/2005 | Skiba | |
| 2005/0227895 A1 | 10/2005 | Ghosh et al. | |
| 2006/0127498 A1 | 6/2006 | Sugiura | |
| 2006/0223962 A1 | 10/2006 | Getman et al. | |
| 2006/0293623 A1 | 12/2006 | Carroll | |
| 2007/0021383 A1 | 1/2007 | Loder | |
| 2007/0038132 A1 | 2/2007 | Kishimoto et al. | |
| 2007/0038243 A1 | 2/2007 | Rutherford | |
| 2007/0042198 A1 | 2/2007 | Schonemyr et al. | |
| 2007/0065475 A1 | 3/2007 | Elfersy | |
| 2007/0088224 A1 | 4/2007 | Friedman et al. | |
| 2007/0129636 A1 | 6/2007 | Friedman et al. | |
| 2007/0166344 A1 | 7/2007 | Qu et al. | |
| 2007/0193822 A1 | 8/2007 | Statner et al. | |
| 2007/0218096 A1 | 9/2007 | Wooley | |
| 2007/0227930 A1 | 10/2007 | Bromberg et al. | |
| 2007/0275929 A1 | 11/2007 | Fuls et al. | |
| 2008/0033329 A1 | 2/2008 | Downs et al. | |
| 2008/0166384 A1 | 7/2008 | Jones | |
| 2008/0171068 A1 | 7/2008 | Wyner et al. | |
| 2008/0193497 A1 | 8/2008 | Samuelsen et al. | |
| 2008/0236596 A1 | 10/2008 | Pierskalla et al. | |
| 2008/0242794 A1 | 10/2008 | Sandford et al. | |
| 2008/0260804 A1 | 10/2008 | Morris et al. | |
| 2008/0264445 A1 | 10/2008 | Levitt et al. | |
| 2009/0074881 A1 | 3/2009 | Kielbania, Jr. | |
| 2009/0196896 A1 | 8/2009 | Patton et al. | |
| 2009/0215917 A1 | 8/2009 | Trotter et al. | |
| 2009/0223411 A1 | 9/2009 | Higgins et al. | |
| 2009/0227454 A1 | 9/2009 | Jaiswal | |
| 2009/0252647 A1 | 10/2009 | Orofino | |
| 2009/0259157 A1 | 10/2009 | Thomas | |
| 2009/0281368 A1 | 11/2009 | Krubsack et al. | |
| 2009/0285890 A1 | 11/2009 | Van Den Plas et al. | |
| 2009/0288908 A1 | 11/2009 | Giroux et al. | |
| 2009/0291147 A1 | 11/2009 | Sandford et al. | |
| 2009/0307843 A1 | 12/2009 | Hookway et al. | |
| 2009/0312684 A1 | 12/2009 | Leonard et al. | |
| 2010/0028462 A1 | 2/2010 | Bolkan et al. | |

(56) References Cited

U.S. PATENT DOCUMENTS

| | | |
|---|---|---|
| 2010/0032231 A1 | 2/2010 | Statner et al. |
| 2010/0056485 A1 | 3/2010 | Park |
| 2010/0063431 A1 | 3/2010 | Bae |
| 2010/0086580 A1 | 4/2010 | Nyman et al. |
| 2010/0089408 A1 | 4/2010 | McCaughey et al. |
| 2010/0113871 A1 | 5/2010 | Dias et al. |
| 2010/0137764 A1 | 6/2010 | Eddy |
| 2010/0159256 A1 | 6/2010 | Yamasaki et al. |
| 2010/0167978 A1 | 7/2010 | Iyer et al. |
| 2010/0197748 A1 | 8/2010 | Schwarz et al. |
| 2010/0255178 A1 | 10/2010 | Leander et al. |
| 2010/0331710 A1 | 12/2010 | Eddy |
| 2011/0084578 A1 | 4/2011 | Newkirk et al. |
| 2011/0124772 A1 | 5/2011 | Wang et al. |
| 2011/0186462 A1 | 8/2011 | Storey et al. |
| 2011/0200655 A1 | 8/2011 | Black et al. |
| 2011/0209835 A1 | 9/2011 | Balbona et al. |
| 2011/0233810 A1 | 9/2011 | Neigel et al. |
| 2011/0236504 A1 | 9/2011 | Hata et al. |
| 2011/0245743 A1 | 10/2011 | Eddy |
| 2011/0250626 A1 | 10/2011 | Williams et al. |
| 2011/0271873 A1 | 11/2011 | Ohlhausen et al. |
| 2011/0282302 A1 | 11/2011 | Lopez et al. |
| 2012/0015200 A1 | 1/2012 | Ali et al. |
| 2012/0021405 A1 | 1/2012 | Palzkill et al. |
| 2012/0052106 A1* | 3/2012 | Eddy ............ A01N 55/00 424/78.37 |
| 2012/0052289 A1 | 3/2012 | Jing et al. |
| 2012/0070481 A1 | 3/2012 | Bolkan et al. |
| 2012/0070509 A1 | 3/2012 | Sugiura |
| 2012/0134953 A1 | 5/2012 | Gentle et al. |
| 2012/0135188 A1 | 5/2012 | Proton |
| 2012/0136313 A1 | 5/2012 | Smith |
| 2012/0157567 A1 | 6/2012 | Ou et al. |
| 2012/0157904 A1 | 6/2012 | Stein |
| 2012/0173274 A1 | 7/2012 | Rensvold et al. |
| 2012/0246788 A1 | 10/2012 | Harrell et al. |
| 2012/0263910 A1 | 10/2012 | Baychar |
| 2012/0296252 A1 | 11/2012 | Cumming et al. |
| 2013/0017242 A1* | 1/2013 | Richardson ......... A01N 25/34 424/411 |
| 2013/0045265 A1 | 2/2013 | Chapman |
| 2013/0101674 A1 | 4/2013 | Toft |
| 2013/0101677 A1 | 4/2013 | Callahan et al. |
| 2013/0231599 A1 | 9/2013 | Eddy |
| 2013/0273132 A1 | 10/2013 | Eddy |
| 2013/0273133 A1 | 10/2013 | Eddy |
| 2013/0338553 A1 | 12/2013 | Eddy |
| 2013/0345170 A1 | 12/2013 | Eddy |
| 2014/0011766 A1 | 1/2014 | Krafft |
| 2014/0051732 A1 | 2/2014 | Ghannoum et al. |
| 2014/0066869 A1 | 3/2014 | Toft |
| 2014/0100504 A1 | 4/2014 | Eddy |
| 2014/0199356 A1 | 7/2014 | Chason et al. |
| 2014/0199358 A1 | 7/2014 | Chason et al. |
| 2014/0199359 A1 | 7/2014 | Chason et al. |
| 2014/0221876 A1 | 8/2014 | Eddy |
| 2014/0256382 A1 | 9/2014 | Eddy |
| 2014/0271794 A1 | 9/2014 | Eddy |
| 2014/0276456 A1 | 9/2014 | Eddy |
| 2014/0302168 A1 | 10/2014 | Perry |
| 2014/0326192 A1 | 11/2014 | Coupe et al. |
| 2014/0352039 A1 | 12/2014 | Abbey et al. |
| 2015/0004361 A1 | 1/2015 | Culpepper |
| 2015/0005684 A1 | 1/2015 | Evans |
| 2015/0011716 A1 | 1/2015 | Lombardi |
| 2015/0024019 A1 | 1/2015 | Ali et al. |
| 2015/0031729 A1 | 1/2015 | Ghannoum et al. |
| 2015/0080827 A1 | 3/2015 | Fogg |
| 2015/0086597 A1 | 3/2015 | Mallak et al. |
| 2015/0089720 A1 | 4/2015 | Abbey et al. |
| 2015/0143615 A1 | 5/2015 | LePage |
| 2015/0158608 A1 | 6/2015 | Talarico |
| 2015/0305343 A1 | 10/2015 | Burke et al. |
| 2015/0328240 A1 | 11/2015 | Hilliard et al. |
| 2015/0352320 A1 | 12/2015 | Eddy |
| 2016/0051389 A1 | 2/2016 | Seligman |
| 2016/0107411 A1 | 4/2016 | Fox et al. |
| 2016/0143275 A1 | 5/2016 | Lan et al. |
| 2016/0143276 A1 | 5/2016 | Lan et al. |
| 2016/0151189 A1 | 6/2016 | Romo et al. |
| 2016/0171179 A1 | 6/2016 | Donofrio et al. |
| 2016/0262382 A1 | 9/2016 | Lan et al. |
| 2016/0262383 A1 | 9/2016 | Lan et al. |
| 2016/0295858 A1 | 10/2016 | Mason et al. |
| 2016/0354005 A1 | 12/2016 | Oakley et al. |
| 2016/0361478 A1 | 12/2016 | Eddy |
| 2017/0000115 A1 | 1/2017 | Nassar et al. |
| 2017/0000651 A1 | 1/2017 | Cumming et al. |
| 2017/0027269 A1 | 2/2017 | Wilson et al. |
| 2017/0081707 A1 | 3/2017 | Dillon et al. |
| 2017/0106622 A1 | 4/2017 | Bonin |
| 2017/0176146 A1 | 6/2017 | Böhringer et al. |
| 2017/0224043 A1 | 8/2017 | Bouchard-Fortin et al. |
| 2017/0236398 A1 | 8/2017 | Eddy et al. |
| 2017/0246041 A1 | 8/2017 | Cumming et al. |
| 2017/0265475 A1 | 9/2017 | Chason et al. |
| 2017/0274114 A1 | 9/2017 | Song et al. |
| 2017/0280716 A1 | 10/2017 | Lan et al. |
| 2017/0319758 A1 | 11/2017 | Eddy et al. |
| 2017/0367899 A1 | 12/2017 | Lundh et al. |
| 2018/0028431 A1 | 2/2018 | Chiattello et al. |
| 2018/0055695 A1 | 3/2018 | Park |
| 2018/0080605 A1 | 3/2018 | Janway et al. |
| 2018/0139571 A1 | 5/2018 | Nassar et al. |
| 2018/0224674 A1 | 8/2018 | Carabin |
| 2018/0243790 A1 | 8/2018 | Grossman et al. |
| 2019/0046081 A1 | 2/2019 | Kilcran et al. |
| 2019/0046082 A1 | 2/2019 | Kilcran et al. |
| 2019/0046083 A1 | 2/2019 | Kilcran et al. |
| 2019/0046084 A1 | 2/2019 | Kilcran et al. |
| 2019/0046364 A1 | 2/2019 | Kilcran et al. |
| 2019/0051137 A1 | 2/2019 | Kilcran et al. |
| 2019/0125774 A1 | 5/2019 | Eddy |
| 2019/0134244 A1 | 5/2019 | Eddy |
| 2019/0166828 A1 | 6/2019 | Storey et al. |
| 2019/0209381 A9 | 7/2019 | Cumming et al. |
| 2019/0216090 A1 | 7/2019 | Alimi et al. |
| 2019/0223445 A1 | 7/2019 | Seo et al. |
| 2019/0254865 A1 | 8/2019 | Eddy |
| 2019/0255210 A1 | 8/2019 | Eddy |
| 2019/0276681 A1 | 9/2019 | Eddy |
| 2019/0289954 A1 | 9/2019 | Baychar |
| 2019/0298479 A1 | 10/2019 | Eddy |
| 2019/0360781 A1 | 11/2019 | Böhringer et al. |
| 2020/0022421 A1 | 1/2020 | Kilbey |
| 2020/0068896 A1 | 3/2020 | Eddy |
| 2020/0071540 A1 | 3/2020 | Eddy |
| 2020/0095775 A1 | 3/2020 | Eddy |
| 2020/0097936 A1 | 3/2020 | Eddy |
| 2020/0281288 A1 | 9/2020 | Eddy |
| 2020/0281774 A1 | 9/2020 | Eddy |
| 2020/0282099 A1 | 9/2020 | Eddy |
| 2021/0052345 A1 | 2/2021 | Eddy |
| 2021/0137120 A1 | 5/2021 | Eddy et al. |
| 2021/0299307 A1 | 9/2021 | Eddy |
| 2021/0299309 A1 | 9/2021 | Eddy |

FOREIGN PATENT DOCUMENTS

| | | |
|---|---|---|
| EP | 1600105 A2 | 11/2005 |
| EP | 2377400 A1 | 10/2011 |
| GB | 2200594 A | 8/1988 |
| KR | 1020060055894 A | 5/2006 |
| RU | 2540478 C1 | 2/2015 |
| RU | 2599004 C1 | 10/2016 |
| WO | 0054587 A1 | 9/2000 |
| WO | 0072850 A1 | 12/2000 |
| WO | 2004087226 A1 | 10/2004 |
| WO | 2005042657 A2 | 5/2005 |
| WO | 2007061625 A2 | 5/2007 |
| WO | 2007076413 A2 | 7/2007 |
| WO | 2008076839 A2 | 6/2008 |
| WO | 2008097599 A2 | 8/2008 |

(56) References Cited

FOREIGN PATENT DOCUMENTS

| WO | 2012037615 A1 | 3/2012 |
|---|---|---|
| WO | 2013102021 A2 | 7/2013 |
| WO | 2016130837 A1 | 8/2016 |

OTHER PUBLICATIONS

"Graft Polymerization onto Wool Pretreated with a Mercaptosilane", Textile Research Journal, Aug. 1996, vol. 66, No. 8, 529-532.

Sickbert-Bennett et al., "Comparative Efficacy of Hand Hygiene Agents in the Reductions of Bacteria and Viruses", 2005, pp. 67-77, vol. 33, No. 2, Association for Professionals in Infection Control and Epidemiology, Inc.

Jimenez et al: "Virucidal activity of a quaternary ammonium compound disinfectant against feline calicivirus: A surrogate for norovirus", AJIC: American Journal of Infection Control, Elsevier, Amsterdam, NL, vol 34, No. 5, Jun. 1, 2006 (Jun. 1, 2006), pp. 269-273.

Anonymous: "Guidance for the Management of Norovirus Infection in Cruise Ships", Jul. 1, 2007 (Jul. 1, 2007), pp. 1-76, Health Protection Agency, United Kingdom.

http://www.bovie.com/germgate-factsheet1.html [retrieved on Jun. 10, 2010].

http://www.andonline.com/and_med.nsf/html/UA-851THW [retrieved on Jun. 10, 2010].

http://www.igenericdrugs.com/?s=Life%20Brand%20Disinfectant%20Wipes [retrieved on Dec. 4, 2012].

http://www.zorotools.com/g/Respirator%20Antimicrobial%20Wipes/00118290 [retrieved on Dec. 4, 2012].

ICU Medical, Inc., "MicroClave Neutral Displacement Connector", 2012, M1-1113 Rev. 10, 4 pages.

ICU Medical, Inc., "Antimicrobial MicroClave Neutral Displacement Connector", 2012, M1-1248 Rev. 04, 2 pages.

Anonymous: "Guide to ship sanitation (third edition)", 2011, pp. iii-155 (total pp. 171), World Health Organization, Switzerland.

Proguard Quaternary Disinfectant (http://www.kellysolutions.com/wa/showA 1.asp?Basic_EPA_ID=6836%2D78&EPA_ID=6836%2D78%2D1677&Product_Name=Quaternary+Disinfectant+Cleaner+ProGuard (downloaded on Jun. 26, 2013)).

Sarah Coleman, To Bandage or Not to Bandage: Decoding Thoroughbred Leg Wrappings, Dec. 22, 2015, pp. 1-4 https://www.paulickreport.com/horse-care-category/the-great-bandage-debate-decoding-thoroughbred-leg-wrappings/ (Year: 2015).

A-Tape Cohesive Crepe Bandage Red (Pack 2) Elastic Self Adhesive (10 cm x 4.5 mtr) hhttps://www.amazon.in/Bandages-Assorted-Colors-Waterproof-Adherent/dp/B01I62O0CM (Year: 2016).

Measurement Canada document (https://www.ic.gc.ca/eic/site/mc-mc.nsf/vwapj/VCF-FCV_CAS-67-63-0.pdf/$file/NCF-FCV_CAS-67-63-0.pdf, accessed Apr. 15, 2016, pp. 1-2).

Mahltig B., Grethe T., Haase H. (Jun. 1, 2018) Antimicrobial Coatings Obtained by Sol-Gel Method. In: Klein L., Aparicio M., Jitianu A. (eds) Handbook of Sol-Gel Science and Technology. Springer, Cham. ("Antimicrobial").

https://www.fullerindustriesllc.com/franklin-cleaning-technology/quasar/.

Federal Institute of Industrial Property, "The International Search Report and the Written Opinion of the International Searching Authority", International Application PCT/IB2018/058595, dated Jan. 24, 2019 (9 pages).

European Patent Office, "Extended European Search Report", European Application No. 19194187.1, dated Nov. 18, 2019 (12 pages).

European Patent Office, "Extended European Search Report", European Application No. 18875379.2, dated Feb. 11, 2021 (6 pages).

Anonymous, 2009, SiSiB PC9911 Antimicrobial, Power Chemical Corp, [online]; downloaded from URL<http://www.powerchemcorp.com/library/public/SiSiB_PC9911.pdf> on Oct. 8, 2013; 2 pages.

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

Aegis Environments, Material Safety Data Sheet Aegis Microbe Shield(TM) Program—AEGIS(TM) Antimicrobial (Typical Application Strength), Midland, Michigan USA, May 12, 2004 (5 pages).

Rutala et al., "Guideline for Disinfection and Sterilization in Healthcare Facilities, 2008," Centers for Disease Control (CDC), Department of Health & Human Services, Feb. 15, 2017 (161 pages).

U.S. Food & Drug Administration (FDA), "Reprocessing Medical Devices in Health Care Settings: Validation Methods and Labeling Guidance for Industry and Food and Drug Administration Staff," Mar. 17, 2015 (44 pages).

European Commission, "Aerosol Dispensers Directive Evaluation—Background document", Sep. 23, 2016, Directorate-General for Internal Market, Industry, Entrepreneurship and SMEs, Belgium (1 page).

Monticello, Robert A., "The Use of Reactive Silane Chemistries to Provide Durable, Non-Leaching Antimicrobial Surfaces", AEGIS Environments, Midland, Michigan USA, Jan. 1, 2010 (77 pages).

* cited by examiner

ANTIMICROBIAL TREATMENT FOR A SURGICAL HEADLAMP SYSTEM

CROSS-REFERENCE TO RELATED APPLICATION

This application is a continuation of and claims priority to U.S. patent application Ser. No. 15/938,934, filed on Mar. 28, 2018 (now U.S. Pat. No. 10,864,058, issued Dec. 15, 2020), entitled "ANTIMICROBIAL TREATMENT FOR A SURGICAL HEADLAMP SYSTEM," the entire disclosures of which are incorporated herein by reference.

BACKGROUND OF THE INVENTION

Surgeons sometimes use a surgical headlamp system while performing surgery. The surgical headlamp system includes a headlamp to illuminate the surgical area. The surgical headlamp system typically further includes a headwear structure and various other accessories supported by the headwear structure, such as a video camera. However, the exterior surfaces of the surgical headlamp system may contain harmful bacteria, microbes, viruses, and the like, which can subsequently be transferred to the patient undergoing the surgery.

BRIEF SUMMARY OF THE INVENTION

According to a first aspect of the present disclosure, a surgical headlight system comprises: a headlamp including an exterior surface; and an antimicrobial coating applied to the exterior surface of the headlamp; wherein, the antimicrobial coating includes a silane quaternary ammonium ion or salt thereof.

Embodiments of the first aspect of the invention can include any one or a combination of the following features:
the silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl) propyldimethyloctadecyl ammonium ion, or 3-(trihydroxysilyl)propyldimethyloctadecyl ammonium chloride;
a headwear structure, configured to be worn on a surgeon's head during surgery, supporting the headlamp, the headwear structure including an exterior surface;
the antimicrobial coating additionally applied to the exterior surface of the headwear structure;
a video camera configured to record a surgery, the video camera including an exterior surface, and the antimicrobial coating applied to the exterior surface of the video camera;
a cable attached to the headlamp and configured to attach to a power source to power the headlamp, the cable including an exterior surface, and the antimicrobial coating applied to the exterior surface of the cable;
a color temperature filter attached to the headlamp, the color temperature filter having an exterior surface, and the antimicrobial coating applied to the exterior surface of the color temperature filter; and
binocular loupes including an exterior surface, and an antimicrobial coating applied to the exterior surface of the binocular loupes.

According to a second aspect of the present disclosure, a method of imparting antimicrobial properties onto an exterior surface of a surgical headlight system comprising: presenting a surgical headlight system including a headlamp including an exterior surface; and applying, to the exterior surface of the headlamp, a solution including a silane quaternary ammonium ion or salt thereof.

Embodiments of the second aspect of the invention can include any one or a combination of the following features:
the silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl) propyldimethyloctadecyl ammonium ion, or 3-(trihydroxysilyl)propyldimethyloctadecyl ammonium chloride;
the solution further includes isopropyl alcohol;
the silane quaternary ammonium ion or salt thereof is between 0.1 percent and 10 percent by weight of the solution;
the isopropyl alcohol is between 30 percent to 90 percent by weight of the solution;
the surgical headlight system further including a headwear structure, configured to be worn on a surgeon's head during surgery, supporting the headlamp, the headwear structure including an exterior surface, applying the solution to the exterior surface of the headwear structure;
the surgical headlight system further including a video camera configured to record a surgery, the video camera including an exterior surface, and applying the solution to the exterior surface of the video camera; and
the surgical headlight system further including a cable attached to the headlamp and configured to attach to a power source to power the headlamp, the cable including an exterior surface, and applying the solution to the exterior surface of the cable.

These and other features, advantages, and objects of the present invention will be further understood and appreciated by those skilled in the art by reference to the following specification, claims, and appended drawings.

DETAILED DESCRIPTION

For purposes of description herein, it is to be understood that the specific devices and processes illustrated in the attached drawings, and described in the following specification are simply exemplary embodiments of the inventive concepts defined in the appended claims. Hence, physical characteristics relating to the embodiments disclosed herein are not to be considered as limiting, unless the claims expressly state otherwise.

Figure 1:
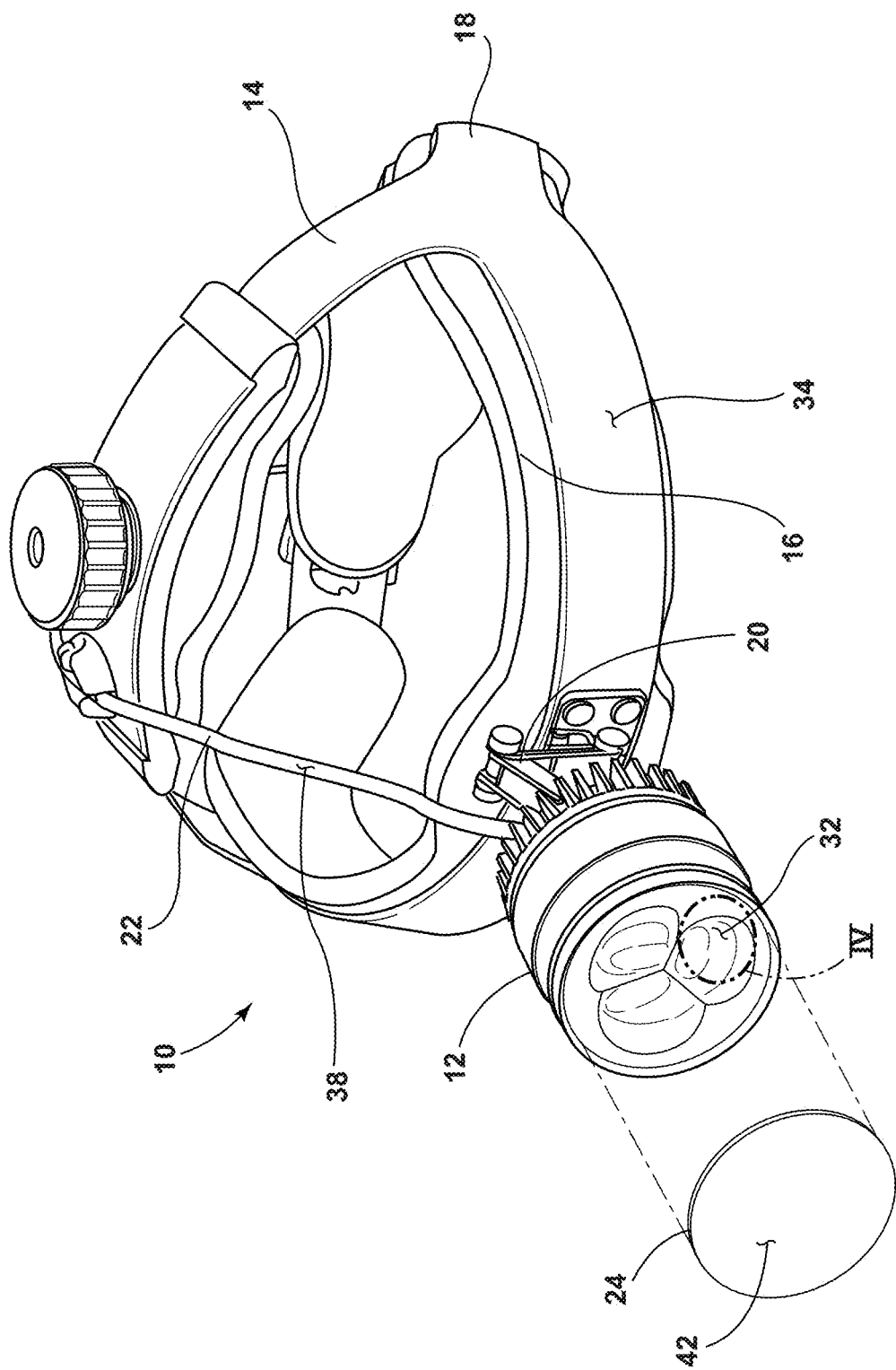
FIG. 1 is a perspective view of a first embodiment of a surgical headlight system, illustrating a headlamp with an exterior surface included thereon.

Referring to FIG. 1, a surgical headlight system 10 includes a headlamp 12. In general terms, the headlamp 12 emits light to illuminate a surgical area on a patient to assist a surgeon in performing a surgical procedure on the patient.

The surgical headlight system 10 further includes a headwear structure 14. The headwear structure 14 is configured to be worn on the surgeon's head during surgery. The headwear structure 14 can include padding 16, which adds comfort to the surgeon wearing the surgical headlight system 10, and a more rigid band 18 to extend around the surgeon's head supporting the padding 16 and the headlamp 12. The headwear structure 14 can support the headlamp 12 via an adjustable arm 20 attaching the headlamp 12 to the headwear structure 14. The surgical headlight system 10 can further include a cable 22. The cable 22 is attached to the headlamp 12 and to a power source (not illustrated, such as a battery) and allows the power source to power the headlamp 12 and thus emit light. The cable 22 can be used for any purpose, however. The surgical headlight system 10 can further include a color temperature filter 24 removably attached to the headlamp 12. The color temperature filter 24 can alter the light emitted by the headlamp 12 so that the light illuminating the surgical area is more beneficial to the surgeon.

Figure 2:
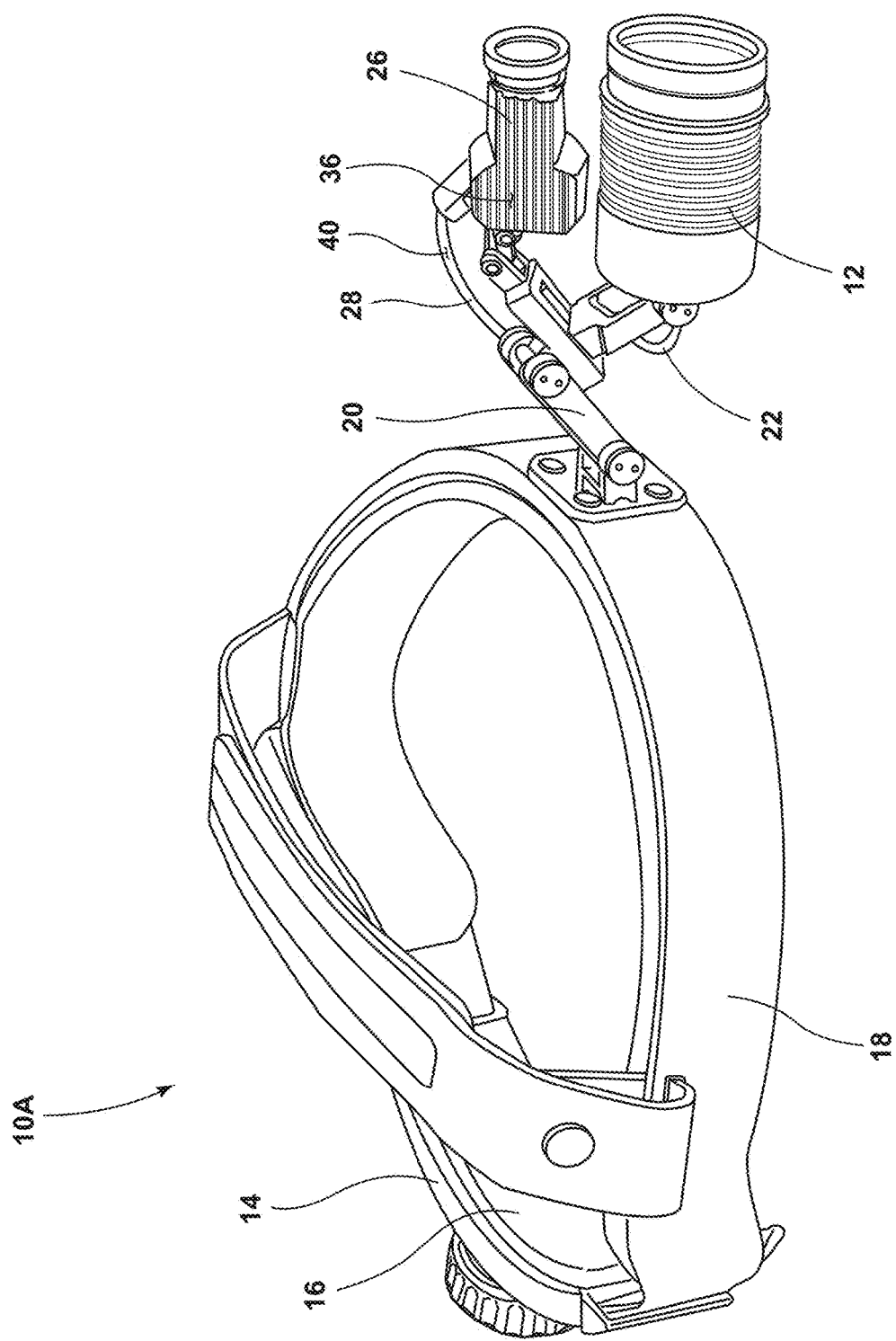
FIG. 2 is a perspective view of a second embodiment of a surgical headlight system, illustrating a video camera with an exterior surface included thereon.

Referring now to FIG. 2, another surgical headlight system 10A is illustrated. This surgical headlight system 10A, like surgical headlight system 10, includes a headwear structure 14 (including padding 16 and a more rigid band 18) supporting a headlamp 12 via an adjustable arm 20. As before, a cable 22 connects the headlamp 12 to a power source (again not illustrated). The surgical headlight system 10A further includes a video camera 26. The video camera 26 is configured to record a surgery and may include a cable 28 for connection to a power source and to transmit data, such as audio and/or video data to an external source.

Figure 3:
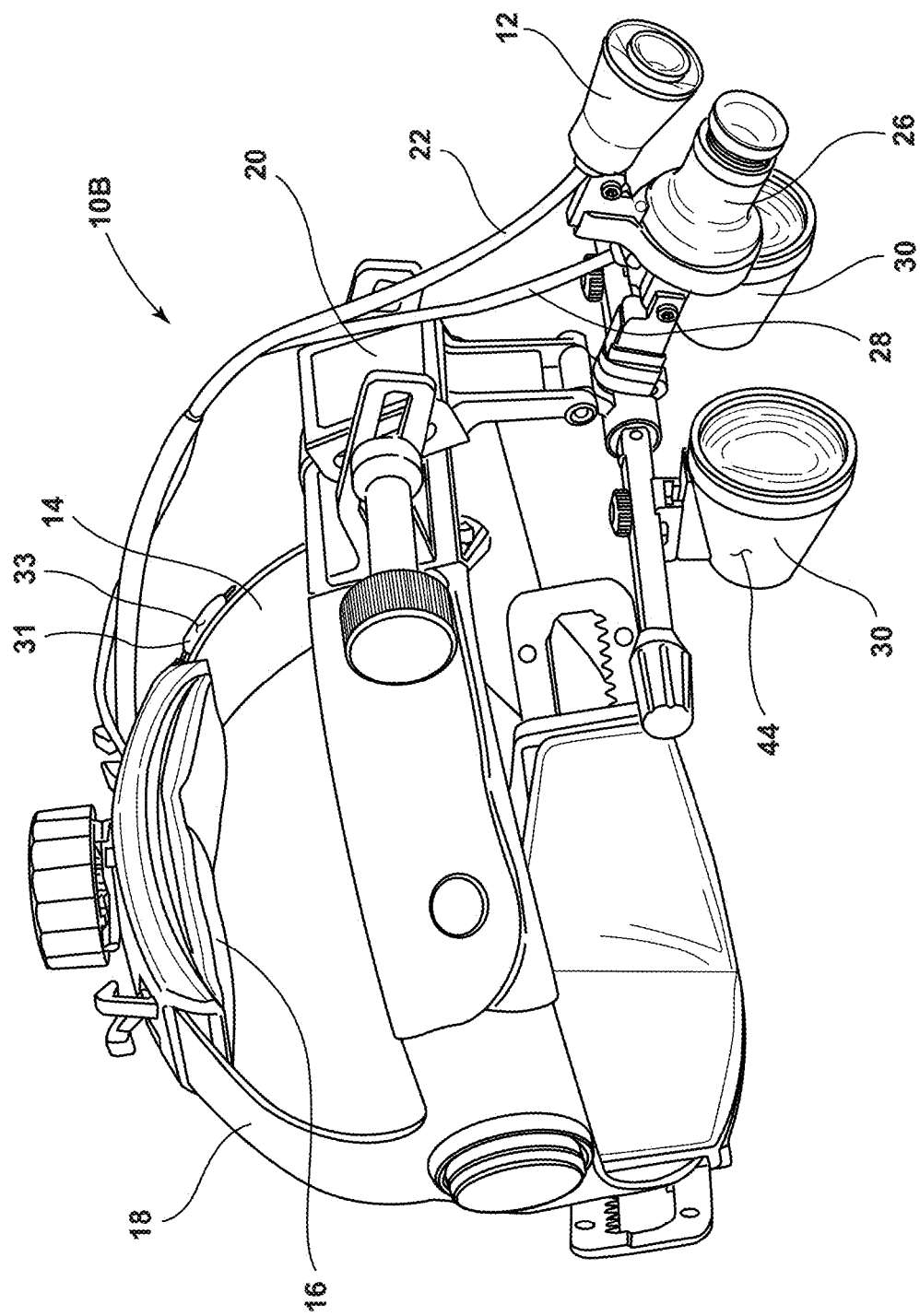
FIG. 3 is a perspective view of a third embodiment of a surgical headlight system, illustrating binocular loupes with an exterior surface included thereon.

Referring now to FIG. 3, another surgical headlight system 10B is illustrated. This surgical headlight system 10B, like surgical headlight systems 10 and 10A, includes a headwear structure 14 (including padding 16 and a more rigid band 18) supporting a headlamp 12 and video camera 26 via an adjustable arm 20. As before, a cable 22 connects the headlamp 12 to a power source (again not illustrated) and a cable 28 connects the video camera 26 to a power source (not illustrated) and can transmit data, such as audio and/or video data to an external source. The surgical headlight system 10B further includes a pair of binocular loupes 30, which magnify the surgical area when the surgeon views through the pair of binocular loupes 30. The adjustable arm 20 additionally connects the binocular loupes 30 to the headwear structure 14. The surgical headlight system 10B further includes a transmitter 31, which can be in communication with the video camera 26 via cable 28 or otherwise and transmit data (such as audio and/or video data) to an external receiver.

The surgical headlight systems 10, 10A, and 10B described above all include a variety of exterior surfaces that may harbor harmful microbes, viruses, bacteria, and the like. For example, headlamp 12 includes an exterior surface 32 (see FIG. 1). Likewise, the headwear structure 14 includes an exterior surface 34, the video camera 26 includes an exterior surface 36 (see FIG. 2), and the cables 22 and 28 each include an exterior surface 38 (see FIG. 1) and 40 (see FIG. 2), respectively. Similarly, the color temperature filter 24 has an exterior surface 42 (see FIG. 1) and the pair of binocular loupes 30 include an exterior surface 44 (see FIG. 3). The transmitter 31 includes an exterior surface 33.

Figure 4:
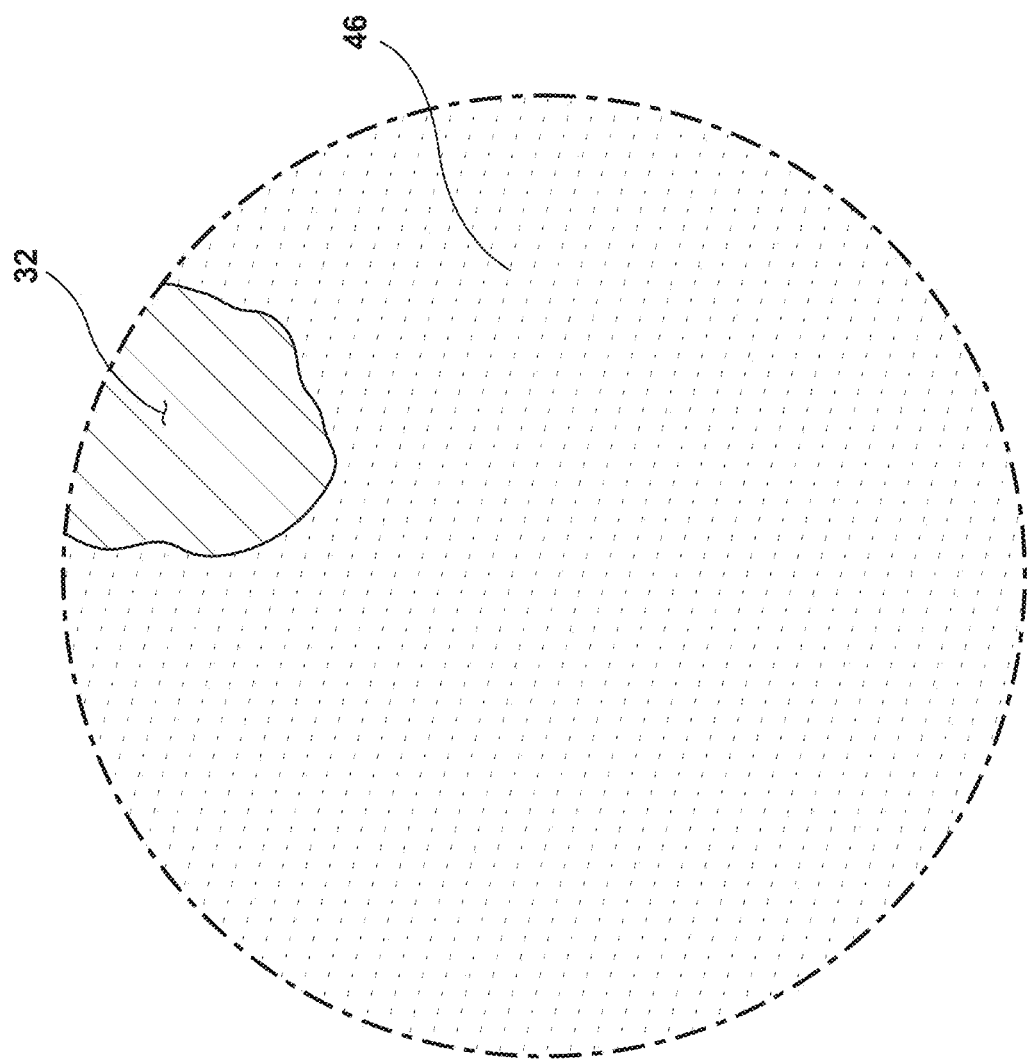
FIG. 4 is a schematic magnified view of area IV from FIG. 1, illustrating an antimicrobial coating applied over the exterior surface of the headlamp of FIG. 1.

Referring now to FIG. 4, the surgical headlight systems 10, 10A, and 10B further include an antimicrobial coating 46 applied to, and at least partially, covering the exterior surface 32 of the headlamp 12. The antimicrobial coating 46 can additionally (or separately) be applied to anything attached to or part of the surgical headlight systems 10, 10A, and 10B. In other words, the antimicrobial coating 46 can be applied to, and at least partially cover, the exterior surface 34 of the headwear structure 14, the exterior surface 36 of the video camera 26, the exterior surface 38 of the cable 22, the exterior surface 40 of the cable 28, the exterior surface 42 of the color temperature filter 24, the exterior surface 44 of the pair of binocular loupes 30, and the exterior surface 33 of the transmitter 31.

The antimicrobial coating 46 includes a silane quaternary ammonium ion or salt thereof. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. Applying the antimicrobial coating 46 to the various exterior surfaces 32, 34, 36, 38, 40, 42, and 44 of the surgical headlight systems 10, 10A, and 10B imparts antimicrobial properties on the various exterior surfaces 32, 34, 36, 38, 40, 42, and 44, which prevents or lessens the ability of said exterior surfaces 32, 34, 36, 38, 40, 42, and 44 to harbor harmful microbes, viruses, bacteria, and the like. Applying the antimicrobial coating 46 to the various exterior surfaces 32, 34, 36, 38, 40, 42, and 44 serves to lessen the ability of the surgical headlight systems 10, 10A, and 10B to act as a vehicle that transmits the harmful microbes, viruses, bacteria, and the like to the patient.

Further described herein is a novel method of imparting antimicrobial properties onto any of the exterior surfaces 32, 34, 36, 38, 40, 42, and 44 of any of the surgical headlight systems 10, 10A, and 10B described above. The method comprises presenting a surgical headlight system 10, 10A, or 10B including the headlamp 12 with the exterior surface 32. The method further comprises applying, to the exterior surface 32 of the headlamp 12, a solution including the silane quaternary ammonium ion or salt thereof, as described above. In addition to the silane quaternary ammonium ion or salt thereof, the solution can further include a solvent. A preferred solvent is isopropyl alcohol.

The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution.

As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

Again, the solution can be applied to any exterior surface of the surgical headlight systems 10, 10A, and 10B described above, including the exterior surface 34 of the headwear structure 14, the exterior surface 36 of the video camera 26, the exterior surface 38 of the cable 22, and so on.

It is to be understood that variations and modifications can be made on the aforementioned structure without departing from the concepts of the present invention, and further it is to be understood that such concepts are intended to be covered by the following claims unless these claims by their language expressly state otherwise.

The invention claimed is:

1. A surgical headlight system comprising:
   a headwear structure configured to be worn on a surgeon's head during surgery, the headwear structure comprising an exterior surface; and
   an antimicrobial coating applied to the exterior surface of the headwear structure;
   wherein, the antimicrobial coating comprises a solution comprising isopropyl alcohol and a silane quaternary ammonium ion or salt thereof.

2. The surgical headlight system of claim 1, wherein the silane quaternary ammonium ion or salt thereof comprises one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

3. The surgical headlight system of claim 1, wherein the solution comprises 0.1 percent to 10 percent by weight silane quaternary ammonium ion or salt thereof.

4. The surgical headlight system of claim 1, wherein the solution comprises 0.75 percent to 5 percent by weight silane quaternary ammonium ion or salt thereof.

5. The surgical headlight system of claim 1, wherein the solution comprises 30 percent to 90 percent by weight isopropyl alcohol.

6. The surgical headlight system of claim 1, wherein the solution comprises 55 percent to 65 percent by weight isopropyl alcohol.

7. The surgical headlight system of claim 1 further comprising:
   a headlamp supported by the headwear structure, the headlamp comprising an exterior surface;
   wherein, the antimicrobial coating is additionally applied to the exterior surface of the headlamp.

8. The surgical headlight system of claim 7 further comprising:
   a cable attached to the headlamp, the cable comprising an exterior surface;
   wherein, the antimicrobial coating is additionally applied to the exterior surface of the cable.

9. The surgical headlight system of claim 7 further comprising:
   a color temperature filter attached to the headlamp, the color temperature filter comprising an exterior surface;
   wherein, the antimicrobial coating is additionally applied to the exterior surface of the color temperature filter.

10. The surgical headlight system of claim 1 further comprising:
    a video camera supported by the headwear structure, the video camera configured to record a surgery and comprising an exterior surface;
    wherein, the antimicrobial coating is additionally applied to the exterior surface of the video camera.

11. The surgical headlight system of claim 1 further comprising:
    binocular loupes connected to the headwear structure via an adjustable arm, the binocular loupes comprising an exterior surface;
    wherein, the antimicrobial coating is additionally applied to the exterior surface of the binocular loupes.

12. The surgical headlight system of claim 1 further comprising:
    a transmitter including an exterior surface;
    wherein, the antimicrobial coating is additionally applied to the exterior surface of the transmitter.

13. A method of imparting antimicrobial properties onto a surgical headlight system comprising:
    applying, to an exterior surface of a headwear structure of a surgical headlight system, a solution comprising isopropyl alcohol and a silane quaternary ammonium ion or salt thereof.

14. The method of claim 13, wherein the silane quaternary ammonium ion or salt thereof comprises one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

15. The method of claim 13, wherein the solution comprises 0.1 percent to 10 percent by weight silane quaternary ammonium ion or salt thereof.

16. The method of claim 13, wherein the solution comprises 0.75 percent to 5 percent by weight silane quaternary ammonium ion or salt thereof.

17. The method of claim 13, wherein the solution comprises 30 percent to 90 percent by weight isopropyl alcohol.

18. The method of claim 13, wherein the solution comprises 55 percent to 65 percent by weight isopropyl alcohol.

19. The method of claim 13 further comprising:
    applying the solution to an exterior surface of a headlamp supported by the headwear structure.

20. The method of claim 13 further comprising:
    applying the solution to an exterior surface of binocular loupes, the binocular loupes connected to the headwear structure via an adjustable arm.

* * * * *